US008822381B2

(12) United States Patent
Koivunen et al.

(10) Patent No.: US 8,822,381 B2
(45) Date of Patent: Sep. 2, 2014

(54) USES OF THAXTOMIN AND THAXTOMIN COMPOSITIONS AS HERBICIDES

(75) Inventors: Marja Koivunen, Davis, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 13/553,677

(22) Filed: Jul. 19, 2012

(65) Prior Publication Data

US 2013/0190175 A1 Jul. 25, 2013

Related U.S. Application Data

(63) Continuation-in-part of application No. 12/650,315, filed on Dec. 30, 2009, now Pat. No. 8,476,195.

(60) Provisional application No. 61/142,179, filed on Dec. 31, 2008, provisional application No. 61/261,504, filed on Nov. 16, 2009.

(51) Int. Cl.

| | |
|---|---|
| ***A01N 57/10*** | (2006.01) |
| ***A01N 43/60*** | (2006.01) |
| ***A01N 43/36*** | (2006.01) |
| ***A01N 57/20*** | (2006.01) |
| ***A01N 37/34*** | (2006.01) |
| ***A01N 43/54*** | (2006.01) |
| ***A01N 65/40*** | (2009.01) |
| ***A01N 43/90*** | (2006.01) |

(52) U.S. Cl.

CPC ................ *A01N 57/20* (2013.01); *A01N 37/34* (2013.01); *A01N 43/54* (2013.01); *A01N 43/36* (2013.01); *A01N 65/40* (2013.01); *A01N 43/90* (2013.01); *A01N 43/60* (2013.01)

USPC ............ 504/128; 504/127; 504/136; 504/296

(58) Field of Classification Search

USPC ................................. 504/136, 128, 127, 296

See application file for complete search history.

(56) References Cited

U.S. PATENT DOCUMENTS

| | | | | |
|---|---|---|---|---|
| 4,309,208 | A * | 1/1982 | Takematsu et al. ........... | 504/190 |
| 4,990,178 | A | 2/1991 | Haneishi et al. | |
| 7,393,812 | B2 | 7/2008 | Gerwick, III et al. | |
| 7,504,244 | B2 | 3/2009 | Szabo et al. | |
| 7,989,393 | B2 | 8/2011 | Kang et al. | |
| 8,476,195 | B2 | 7/2013 | Koivunen et al. | |
| 2004/0102320 | A1 | 5/2004 | Grimm | |
| 2004/0192551 | A1 | 9/2004 | Bessette | |
| 2008/0248956 | A1 | 10/2008 | Kang et al. | |
| 2009/0099022 | A1 | 4/2009 | Fernandez et al. | |
| 2010/0267560 | A1 | 10/2010 | Leep et al. | |
| 2013/0217573 | A1 | 8/2013 | Koivunen et al. | |
| 2013/0288896 | A1 | 10/2013 | Koivunen et al. | |
| 2013/0296169 | A1 | 11/2013 | Koivunen et al. | |

FOREIGN PATENT DOCUMENTS

| | | |
|---|---|---|
| WO | WO 2013/066894 | 10/2008 |
| WO | WO 2008124675 | 10/2008 |
| WO | WO 2010066677 | 6/2010 |
| WO | WO 2010078452 | 7/2010 |

OTHER PUBLICATIONS

U.S. Appl. No. 13/840,975, Huazhang Huang et al.

Beausejour, "Production of Thaxtomin A by *Streptomyces scabies* Strains in Plant Extract Containing Media," *Can. J. Microbiol.* 45:764-768 (1999).

Duke, "Natural Products as Sources of Herbicides: Current Status and Future Trends," *Weed Res.* 40:99-111 (2000).

Duke, "United States Department of Agriculture—Agricultural Research Service Research on Natural Products for Pest Management," *Pest Management Sci.* 59:708-717 (2003).

Duval, "Thaxtomin A Induces Programmed Cell Death in *Arabidopsis thaliana* Suspension-Cultured Cells," *Planta* 222:820-831 (2006).

Fry, "Thaxtomin A: Evidence for a Plant Cell Wall Target," *Physiolog. Molec. Plant Pathol.* 60:1-8 (2002).

Healy, "The txtAB Genes of the Plant Pathogen *Streptomyces acidiscabies* Encode a Peptide Synthetase Required for Phytotoxin Thaxtomin A Production and Pathogenicity," *Molec. Microbiol.* 38:794-804 (2000).

Hiltunen, "Influence of Thaxtomins in Different Combinations and Concentrations on Growth of Micropropagated Potato Shoot Cultures," *J. Agric. Food Chem.* 54:3372-3379 (2006).

Hoagland, "Microbial Allelochemicals and Pathogens as Bioherbicidal Agents," *Weed Technol.* 15:835-857 (2001).

Johnson, "Plant-Pathogenic *Streptomyces* Species Produce Nitric Oxide Synthase-Derived Nitric Acid in Response to Host Signals," *Chemistry & Biology* 15:43-50 (2007).

King, "Isolation and Characterization of Phytotoxins Associated with *Streptomyces scabies*," *J. Chem. Soc. Chem. Commun.* 13:849-850 (1989).

King, "Chemnistry of Phytotoxins Associated with *Streptomyces scabies*, the Causal Organism of Potato Common Scab," *J. Agric. Food Chem.* 40:834-837 (1992).

King, "Herbicidal Properties of the Thaxtomin Group of Phytotoxins," *J. Agric. Food Chem.* 49:2298-2301 (2001).

King, "More Chemistry of the Thaxtomin Phytotoxins," *Phytochemistry* 64:1091-1096 (2003).

(Continued)

*Primary Examiner* — John Pak
*Assistant Examiner* — Andriae M Holt
(74) *Attorney, Agent, or Firm* — Ying-Horng Liu

(57) ABSTRACT

There is a need for a selective, low-risk herbicide that can be used to control weeds in cereal cultures and turf. The present invention discloses that a bacterial secondary metabolite, thaxtomin and optionally another herbicide is an effective herbicide on broadleaved, sedge and grass weeds. Thaxtomin A and structurally similar compounds can be used as natural herbicides to control the germination and growth of weeds in cereal, turf grass, Timothy grass and pasture grass cultures with no phytotoxicity to these crops. As a natural, non-toxic compound, thaxtomin can be used as a safe alternative for weed control in both conventional and organic farming and gardening systems.

16 Claims, 1 Drawing Sheet

(56) References Cited

OTHER PUBLICATIONS

Koivunen, "Evaluation of a New Natural Product Herbicide for Rice Weed Control," *Proceedings of the California Weed Science Society* 61:113 (2009).
Loria, "Differential Production of Thaxtomins by Pathogenic *Streptomyces* Species in Vitro," *Phytopathology* 85:537-541 (1995).
Scheible, "An *Arabidopsis* Mutant Resistant to Thaxtomin A, a Cellulose Synthesis Inhibitor from *Streptomyces* Species," *The Plant Cell* 15:1781-1794 (2003).
Taylor, "Casoron, A New Aquatic Herbicide," *Hyacinth Control Journal/J. of Aquatic Plant Management* 5:20-21 (1966), available at www.apms.org/japm/vol05/v5p20.pdf.
Examination Report for NZ App. No. 596336 (Aug. 23, 2012).
Examination Report for NZ App. No. 598365 (Aug. 23, 2012).
Extended Search Report for EP App. No. 098371743 (May 12, 2012).
Extended Search Report for EP App. No. 10765219.0 (Jul. 23, 2012).
International Search Report and Written Opinion for PCT App No. PCT/US2009/069856 (Aug. 13, 2010).
International Search Report and Written Opinion for PCT App. No. PCT/US2010/031317 (Nov. 11, 2010).
International Preliminary Report on Patentability for PCT App. No. PCT/US2010/031317 (Oct. 18, 2011).
Office Action (Final Rejection) for U.S. Appl. No. 12/761,382 (Dec. 22, 2011).
Office Action (Non-Final Rejection) for U.S. Appl. No. 12/761,382 (Oct. 5, 2012).
International Search Report and Written Opinion for PCT App. No. PCT/IB2013/002214 dated Jan. 28, 2014 (14 pages).

* cited by examiner

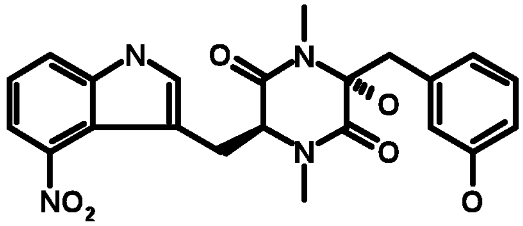

USES OF THAXTOMIN AND THAXTOMIN COMPOSITIONS AS HERBICIDES

PRIORITY CLAIM

This application is a continuation-in-part of application Ser. No. 12/650,315, the contents of which are incorporated herein by reference. application Ser. No. 12/650,315 claims priority from U.S. application Ser. Nos. 61/142,179, filed Dec. 31, 2008 and 61/261,504 filed Nov. 16, 2009 under 35 USC 119(e), in which the contents of both are incorporated herein by reference and also claims priority from Taiwan Patent application no. 098144895, filed Dec. 25, 2009 under 35 USC 119(a)-(d), the contents of which are also incorporated herein by reference.

REFERENCE TO GOVERNMENT GRANT

This invention was supported in part by funds obtained from the U.S. Government (USDA SBIR Grant Number: 2011-33610-30455). The U.S. Government may have certain rights in the invention.

FIELD OF THE INVENTION

This invention relates to compositions and methods for controlling the germination and growth of broadleaf, sedge and grass weeds using compounds comprising thaxtomin, a cyclic dipeptide produced by *Streptomyces* sp., as an active ingredient.

BACKGROUND OF THE INVENTION

Natural products are substances produced by microbes, plants, and other organisms. Microbial natural products offer an abundant source of chemical diversity, and there is a long history of utilizing natural products for pharmaceutical purposes. However, secondary metabolites produced by microbes can also be successfully used for weed and pest control in agricultural applications.

Thaxtomins (4-nitroindol-3-yl-containing 2,5-dioxopiperazines) are a family of dipeptide phytotoxins produced by plant-pathogenic *Streptomyces* sp. (*S. scabies, S. acidiscabies*) that cause scab diseases in potato (*Solanum tuberosum*) (King, Lawrence et al. 1992). Toxin production occurs in diseased tissue and can also be elicited in vitro in an optimal growth medium containing oat bran (Loria, Bukhalid et al. 1995; Beauséjour, Goyer et al. 1999). King and her coworkers (King, Lawrence et al. 2001) demonstrated that all plant pathogenic species in the *Streptomyces* family produce one or more thaxtomins with herbicidal activity. Hiltunen et al. (Hiltunen, Laakso et al. 2006) purified four thaxtomin analogs (thaxtomin A, thaxtomin A ortho isomer, thaxtomin B and thaxtomin D) from cultures of *S. scabies* and *S. turbidiscabies* and showed that all four compounds induced similar symptoms of reduced shoot and root growth, root swelling, (at 10-200 ppb) and necrosis (at 200-1000 ppb) on micropropagated in vitro cultures of potato. In addition, thaxtomins applied in combinations, showed additive effects, but no synergism (Hiltunen, Laakso et al. 2006). According to Duke et al. (Duke, Baerson et al. 2003), both thaxtomin A (FIG. 1) and thaxtomin D have marked activity as pre and post emergent, non-systemic herbicides, and concentrations of less than 1 uM of thaxtomin A causes cell swelling, necrosis and growth inhibition in mono and dicotyledonous seedlings (Healy, Wach et al. 2000). Thaxtomin has been evaluated as an herbicide by Dow Agro Sciences, Inc., and while active, it lacked systemic action (King, Lawrence et al. 2001). The presence of the nitro group in the indole ring required for an L,L- configuration of the diketopiperazine appears to be the minimal requirement for phytotoxicity. The position of the nitro group in the indole ring is very site specific, and the phenyl portion of the phenylalanine plays a necessary role in structural requirements of phytotoxicity (King, Lawrence et al. 1989; King, Lawrence et al. 1992; King, Lawrence et al. 2003). The herbicidal mode of action is based on disruption of cell wall synthesis (Fry and Loria 2002), with inhibition of cellulose biosynthesis being the main target (King et al., 2001; Duval et al., 2005; Johnson et al. 2007). Recently, Kang et al. (Kang, Semones et al. 2008) have described the use of thaxtomin and thaxtomin compositions as algaecides to control algae in water environments.

SUMMARY OF THE INVENTION

The present invention discloses the use of thaxtomin as a pre or post-emergence herbicide against most common weeds in the cereal, pasture grass, Timothy grasses and turf grass, residential gardens, vineyards, orchards and park growth systems. A "growth system" may be any ecosystem for growing cereal, pasture grass, Timothy grass and turf grass. For example, a "cereal growth system" may be a cereal growth culture or may be a field containing planted cereal crops or cereal seeds. Similarly, a "turf grass growth system" may be a turf grass growth culture or may be a field, lawn or golf course containing planted turf grass or turf grass seeds. It can serve as a safer alternative to synthetic herbicides now on the market. A primary object of the invention is to provide novel herbicidal compositions against both broadleaf, sedge and grassy weeds, which include but are not limited to *Chenopodium* sp. (e.g., *Chenopodium album*), *Abutilon* sp. (e.g., *Abutilon theophrasti*), *Helianthus* sp. (e.g., *Helianthus annuus*), *Ambrosia* sp. (e.g., *Ambrosia artemesifolia*), *Amaranthus* sp. (e.g., *Amaranthus retroflexus*),*Convolvulu* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum*), *Malva* sp. (e.g., *Malva neglect*), *Setaria* sp. (e.g., *Setaria lutescens*), *Bromus* sp. (e.g., *Bromus tectorum*), *Poa* sp. (e.g., *Poa annua, Poa pratensis*), *Lollium* sp. (e.g., *Lolium perenne* L. var. Pace), *Festuca* sp. (e.g., *Festuca arundinaceae*) *Schreb*. Sp. (e.g., *Schreb*. var. Aztec II, Anthem II, LS 1100), *Echinochloa* sp. (e.g., *Echinochloa crus-galli*), and particularly, Lambsquarter—*Chenopodium album*, Redroot Pigweed—*Amaranthus retroflexus*, Wild Mustard—*Brassica kaber*, Dandelion—*Taraxacum officinale*, and Black Nightshade—*Solanum nigrum*, that contains thaxtomin as an active ingredient. Another object is to provide a safe, non-toxic herbicidal composition that does not harm cereal crops, pasture grass, Timothy grass or turf grass and a method that will not harm the environment.

The above and other objects are accomplished by the present invention which is directed to herbicidal compositions containing at least one herbicidal agent, e.g., thaxtomin with optionally certain carriers to control the growth and germination of weeds in the cereal growth system and/or turf grass growth system and/or Timothy grass growth system and/or pasture grass growth system. In particular, the invention is further directed to an herbicidal composition for use in modulating the germination and growth of monocotyledonous and/or dicotyledenous and/or sedge weeds in a cereal growth system. In a particular embodiment, the cereal growth system is a non-rice cereal growth system comprising at least one herbicide in which said herbicide is thaxtomin. The compositions of the present invention may further comprise a carrier and/or diluent. In a particular embodiment, the composition is an aqueous composition. In another particular embodiment, the thaxtomin in the composition is dissolved in a diluent comprising an organic solvent such as ethanol, isopropanol, or an aliphatic ketone such as acetone, methyl ethyl ketone, methyl isobutyl ketone.

In a related aspect, the invention is directed to the use of at least one herbicidal agent, e.g., thaxtomin, in the formulation of an herbicide for modulating monocotyledonous and/or dicotyledenous and/or sedge weeds in a cereal growth system, e.g., a non-rice cereal growth system. Similarly, the invention is directed to the use of at least one herbicidal agent in formulation of an herbicide for modulating monocotyledonous and/or dicotyledenous and/or sedge weeds in a turf grass growth system and/or Timothy grass growth system and/or pasture grass growth system, wherein at least one herbicidal agent is thaxtomin.

The compositions of the present invention may comprise in addition to thaxtomin, at least one or more herbicides. Thus the invention may comprise a thaxtomin and a chemical herbicide and/or bioherbicide. Compositions comprising thaxtomin and at least a second herbicide may be used in cereal growth systems (e.g., wheat, triticale, barley, oats, rye, corn, sorghum, sugarcane, rice or millet) and/or turf grass growth systems and/or Timothy grass growth systems and/or pasture grass growth systems and/or residential gardens, vineyards, orchards and park systems and/or aquatic systems. In a particular embodiment these compositions may be used to modulate growth of broadleaf, sedge and grassy weeds, which include but are not limited to *Chenopodium* sp. (e.g., *Chenopodium album*), *Abutilon* sp. (e.g., *Abutilon theophrasti*), *Helianthus* sp. (e.g., *Helianthus annuus*), *Ambrosia* sp. (e.g., *Ambrosia artemesifolia*), *Amaranthus* sp. (e.g., *Amaranthus retroflexus*), *Convolvulu* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum*), *Malva* sp. (e.g., *Malva neglect*), *Setaria* sp. (e.g., *Setaria lutescens*), *Bromus* sp. (e.g., *Bromus tectorum*), *Poa* sp. (e.g., *Poa annua, Poa pratensis*), *Lollium* sp. (e.g., *Lollium perenne* L. var. Pace, *Lollium arundinaceum* (*Schreb.*) var. Atec II or Anthem II), *Festuca* sp. (e.g., *Festuca arundinaceae*) *Schreb*. Sp., *Echinochloa* sp. (e.g., *Echinochloa crus-galli*). The compositions may also be used to modulate growth of aquatic weeds which include but are not limited to *Ammania* sp., *Alisma plantago-aquatica, Cyperus* sp., *Leptochloa* sp.

Given that the invention is directed to the use of thaxtomin as a pre- or post-emergence herbicide, the invention is directed to a method for selectively modulating germination and growth of monocotyledonous, dicotyledonous and sedge weeds in a cereal crop growth system. In a particular embodiment, the cereal growth system is a non-rice cereal crop growth system comprising applying to said weeds or soil in said cereal crop growing system at least one herbicidal agent, wherein said herbicidal agent is thaxtomin, in an amount of effective to modulate germination and growth of said weeds but not modulate growth of cereal crop in said cereal crop growth system. The cereal crop may include but is not limited to corn, wheat, triticale, barley, rye, oats, sorghum, sugarcane, and millet. The invention is further directed to a method for modulating germination and growth of monocotyledonous, dicotyledonous and sedge weeds in a turf, pasture and/or Timothy grass growth system comprising applying to said weeds or soil in said turf grass growing system at least one herbicidal agent, wherein said herbicidal agent is thaxtomin, in an amount of effective to modulate growth of said weeds but not modulate germination and growth of turf grass in said turf grass growth system, pasture grass in said pasture grass growth system and/or Timothy grass in said Timothy grass growth system. The turf grass may be selected from the group consisting of *Festuca* sp., *Poa* sp., *Bromus* sp., *Lolium* sp., *Agrostis* sp., *Zoysia* sp., *Cynodon* sp.

Further, the invention is directed to a method for modulating germination and growth of weeds selected from the group consisting of *Chenopodium* sp. (e.g., *Chenopodium album*), *Abutilon* sp. (e.g., *Abutilon theophrasti*), *Helianthus* sp. (e.g., *Helianthus annuus*), *Ambrosia* sp. (e.g., *Ambrosia artemesifolia*), *Amaranthus* sp. (e.g., *Amaranthus retroflexus*), *Convolvulu* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum*), *Malva* sp. (e.g., *Malva neglect*), *Setaria* sp. (e.g., *Setaria lutescens*), *Bromus* sp. (e.g., *Bromus tectorum*), *Poa* sp. (e.g., *Poa annua, Poa pratensis*), *Lollium* sp. (e.g., *Lollium perenne* L. var. Pace, *Lollium arundinaceum* (*Schreb.*) var. Atec II or Anthem II), *Festuca* sp. (e.g., *Festuca arundinaceae*) *Schreb.* Sp., *Echinochloa* sp. (e.g., *Echinochloa crus-galli*), comprising applying to said weeds or soil an amount of thaxtomin or salt thereof and optionally a second herbicidal agent effective to modulate said germination and growth of said weeds.

As noted above, the method of the present invention may also involve the use of at least a second herbicidal agent. The two herbicidal agents may be applied together in one formulation or separately in two formulations. Control of weeds can be achieved by using thaxtomin A in a tank mix or rotation with other herbicidally active compounds known to have good activity against grass weeds but no or low phytotoxicity against cereal crops and/or turf grass and/or, pasture grass and/or Timothy grasses. In particular, the invention relates to a method for modulating growth of monocotyledonous, dicotyledonous and sedge weeds comprising applying to said weeds an amount of thaxtomin and amount of at least a second herbicidal agent to modulate growth of said weeds. The two herbicidal agents may be applied together in one formulation or separately in two formulations. The thaxtomin and second herbicidal agent may be applied in a cereal growth system (e.g., wheat, triticale, barley, oats, rye, corn, sorghum, sugarcane, rice or millet) and/or turf grass growth system and/or pasture grass growth system and/or Timothy grass growth system.

BRIEF DESCRIPTION OF THE FIGURES

FIG. 1 shows the structure of Thaxtomin A.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Thaxtomin utilized in this invention may be derived in fermentation of the following actinomycetes cultures: *S. scabies*—ATCC 49173, *S. acidiscabies*—ATCC 49003 and BL37-EQ-010—or it can be purchased from commercial sources.

The thaxtomin utilized in the invention include but are not limited to agents described as cyclic dipeptides having the basic structure cyclo-(L-4-nitrotryptophyl-L-phenylalanyl). In embodiments, suitable diketopiperazne moieties may be N-methylated, and include congeners carrying phenylalanyl alpha and ring-carbon hydroxyl groups. The chemical in a particular embodiment comprises:

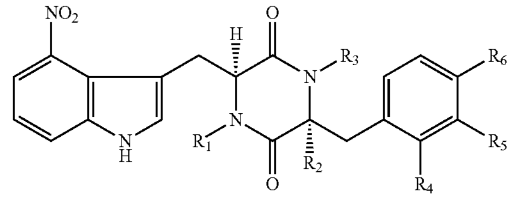

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, and combinations thereof.

Non limiting examples of suitable thaxtomin is for use in accordance with the present invention include but are not limited to thaxtomin A, thaxtomin A ortho isomer, thaxtomin B, thaxtomin C, hydroxythaxtomin C, thaxtomin A p-isomer, hydroxythaxtomin A and des-N-methylthaxtomin C and derivatives of any of these (See FIG. 1).

The compositions of the present invention may be sprayed on the plant or applied to soil. Particular embodiments are described in the Examples, infra. These compositions may be in the form of dust, coarse dust, micro granules, granules, wettable powder, emulsifiable concentrate, liquid preparation, suspension concentrate, water degradable granules or oil suspension.

The compositions of the invention do comprise a carrier and/or diluent. The term, 'carrier' as used herein means an inert, organic or inorganic material, with which the active ingredient is mixed or formulated to facilitate its application to plant or other object to be treated, or its storage, transport and/or handling. Examples of diluents or carriers for the pre- and post-emergence herbicides include, but are not limited to, water, milk, ethanol, mineral oil, glycerol.

The compositions of the present invention may comprise at least two herbicidal agents. One herbicidal agent is thaxtomin set forth above. It may be present in one embodiment thaxtomin is present in an amount ranging from about 0.01 to about 5.0 mg/mL. The other herbicidal agent may be a bioherbicide and/or a chemical herbicide. The bioherbicide may be derived from a plant or may be a microbial bioherbicide. In particular, the bioherbicide derived from a plant may be derived from pepper (e.g., sarmentine) or may be a plant essential oil (e.g., lemongrass oil). The microbial bioherbicide may be derived from bacteria (e.g. *Streptomyces* sp.) or fungus. The bioherbicide may be selected from the group consisting of clove, cinnamon, lemongrass, citrus oils, orange peel oil, bialaphos, cornexistin, AAL-toxin, leptospermone, sarmentine, sarmentine analog momilactone B, sorgoleone, ascaulatoxin, manuka oil, *Phoma macrostoma*, m-tyrosine, chelated iron and ascaulatoxin aglycone. In a particular embodiment, the composition may comprise thaxtomin, lemongrass oil and optionally a surfactant and/or vegetable oil. In another embodiment, the composition may comprise thaxtomin, sarmentine and optionally a nonionic surfactant and/or vegetable oil. In another particular embodiment, the composition may comprise thaxtomin, bialaphos (also known as bialafos) and optionally a nonionic surfactant and/or vegetable oil. The bioherbicide such as lemongrass oil, bialaphos (bialfos) or sarmentine may be present in an amount ranging from about 0.1 mg/mL to about 100 mg/mL and more preferably between about 0.5 mg/mL to about 50 mg/mL.

The chemical herbicide may be selected from the group consisting diflufenzopyr and salts thereof, dicamba and salts thereof, topramezone, tembotrione, S-metolachlor, atrazine, mesotrione, primisulfuron-methyl, 2,4-dichlorophenoxyacetic acid, nicosulfuron, thifensulfuron-methyl, asulam, metribuzin, diclofop-methyl, fluazifop, fenoxaprop-p-ethyl, asulam, oxyfluorfen, rimsulfuron, mecoprop, and quinclorac, thiobencarb, clomazone, cyhalofop, propanil, bensulfuron-methyl, penoxsulam, triclopyr and triclopyr-ester, trifloxysulfuron-sodium, imazethapyr, halosulfuron-methyl, pendimethalin, bispyribac-sodium, carfentrazone ethyl, sodium bentazon/sodium acifluorfen, glufosinate, glyphosate and orthosulfamuron, as well as a member of the dinitroaniline family, which includes but is not limited to pendimenthalin, oryzalin, trifuralin, etc., as well as members of the pyridine, phenylurea, chloroacetamide and triazine families, among others.

The chemical herbicide such as pendimethalin or clomazone, atrazine, oryzalin, trifluralin and metolachlor may be present in a pre-emergent weed control application in an amount ranging from about 0.1 mg/mL to about 50 mg/mL and a chemical herbicide such as cyhalofop, S-metolachlor, bispyribac-sodium, glyophosate, glufosinate, mesotione, penoxsulam, carfentrazone, quinclorac, triclopyr-ester, trioxysulfuron-sodium, thiobencarb, propanil, 2,4-D, dicamba in a post-emergent application from about 0.1 mg/mL to about 50 mg/mL. The composition may further comprise an adjuvant which may be vegetable oil comprising ethyl oleate, polyethylene dialkyl ester and ethoxylated nonylphenol. The composition may additionally comprise a surfactant to be used for the purpose of emulsification, dispersion, wetting, spreading, integration, disintegration control, stabilization of active ingredients, improvement of fluidity or rust inhibition. The choice of dispersing and emulsifying agents, such as nonionic, anionic, amphoteric and cationic dispersing and emulsifying agents, and the amount employed is determined by the nature of the composition and the ability of the agent to facilitate the dispersion of the herbicidal compositions of the present invention.

For post-emergent formulations, the formulation components used may contain smectite clays, attapulgite clays and similar swelling clays, thickeners such as xanthan gums, gum Arabic and other polysaccharide thickeners as well as dispersion stabilizers such as nonionic surfactants (for example polyoxyethylene (20) monolaurate or polysorbate 60 POE (20) sorbitan monostearate, ethylene glycol monostearate). The concentration of the clays may vary between about 0-2.5% w/w of the total formulation, the polysaccharide thickeners may range between about 0-0.5% w/w of the total formulation and the surfactants may range from about 0-5% w/w of the total formulation.

EXAMPLES

The composition and method of the present invention will be further illustrated in the following, non-limiting Examples. The examples are illustrative of various embodiments only and do not limit the claimed invention regarding the materials, conditions, weight ratios, process parameters and the like recited herein.

Example 1

In a pot study test in greenhouse conditions, 6-inch corn plants (*Zea mays* var. Sunglow) were sprayed with increasing concentrations of thaxtomin A mixed in a carrier 4% ethanol, 0.02% polysorbate 60 POE (20) sorbitan monostearate solution. The spraying solutions contained 0.125, 0.25, 0.5 and 1.0 mg thaxtomin A/mL, and the plants are sprayed until total coverage. Each treatment was done in three replicates, and a control solution consists of water with 4% ethanol and 0.02% polysorbate 60 POE (20) sorbitan monostearate as a surfactant. Prior to and after treatments, plants are grown in a greenhouse under artificial lights (12-h light/dark cycle) at 25° C.

Plants are evaluated in one-week intervals starting at 7 days after treatment. The final evaluation is done three weeks after treatment, at which time point, no phytotoxicity is observed in any of the test plants even at the highest thaxtomin A concentration.

Example 2

A pot study is conducted to test the phytotoxicity of thaxtomin A on corn (*Zea mays* var. Early Sunglow) and wheat (*Triticum aestivum* var. PR1404). To confirm the activity on broadleaf weeds, pigweed (*Amaranthus* sp.) is planted in the same pot with either three corn or five wheat seeds, and sprayed simultaneously with the cereal test plants. The less than 3-inch tall plants grown under growth lights (12-h light/12-h dark) at 28° C. are sprayed with thaxtomin A solutions derived from a liquid culture of *S. acidiscabies* containing 0.5, and 1.0 mg thaxtomin A per mL of solvent (4% ethanol and 0.2% non-ionic surfactant). A solution of 4% ethanol+0.2% non-ionic surfactant without thaxtomin A is used as a control treatment. Each treatment is conducted in three replicates. Treated plants are kept at 28° C. under growth lights and observed at three time points—7, 14 and 21 days after treatment—for visual symptoms of phytotoxicity on corn and wheat and % control of pigweed.

At each time point, no symptoms of phytotoxicity are observed in the cereal plants treated with thaxtomin A. The highest concentration of thaxtomin A (1.0 mg/mL) results in a complete control of pigweed grown in the same pots with corn and wheat.

Example 3

To test the phytotoxicity of thaxtomin A on sorghum plants, five seeds of sorghum (*Sorghum bicolor*) are planted in each 4"×4" plastic pot filled with soil. Plants were grown under optimal conditions in a greenhouse before and after treatment with solutions containing 0.5 and 1.0 mg thaxtomin A /mL. At the time of the treatment, the plants are about 3 inches tall. Each treatment is applied in three replicates, and a control treatment included plants treated with just the carrier (4% EtOH, 0.02% polysorbate 60 POE (20) sorbitan monostearate). Evaluations for phytotoxicity are performed at 7-day intervals starting one week after treatment. The last evaluation is performed three weeks after the treatment at which point, no phytotoxicity is observed in the treated plants in any treatment concentration.

Example 4

A strain of *S. acidiscabies* (ATCC-49003) is grown in oat bran broth for 5 days (25° C., 200 rpm). The whole cell broth with thaxtomin A is extracted using XAD resin. The dried crude extract was resuspended in 4% ethanol and 0.02% non-ionic surfactant at a concentration of 10 mg/mL, and the solutions with two different concentrations of thaxtomin A (0.5 and 1.0 mg/mL) are tested the following broadleaf weed species:

Lambsquarter—*Chenopodium album*
Velvetleaf—*Abutilon theophrasti*
Sunflower—*Helianthus annuus*
Ragweed, Common—*Ambrosia artemesifolia*
Pigweed, Redroot—*Amaranthus retroflexus*
Bindweed, Common—*Convolvulus arvensis*
Mustard, Wild—*Brassica kaber*
Dandelion—*Taraxacum officinale*
Nightshade, Black—*Solanum nigrum*
Mallow, Common—*Malva neglecta* and on the following grass weed species:

Foxtail—*Setaria lutescens*
Brome, Downy—*Bromus tectorum*
Bluegrass, Annual—*Poa annua*
Bluegrass, Kentucky—*Poa pratensis*
Ryegrass, Perennial—(*Lolium perenne* L. var. Pace)
Fescue, Tall—(*Festuca arundinaceae Schreb*. var. Aztec II, Anthem II, LS1100)
Barnyard Grass—*Echinochloa crus-galli*

All plant species are tested in 4"×4" plastic pots in three replicates. The untreated control plants are sprayed with the carrier solution (4% Ethanol, 0.02% glycosperse) and the positive control plants with Roundup at a rate corresponding to 1 fl. oz/acre. Treated plants are kept in a greenhouse under 12h light/12h dark conditions. Data for broadleaf species from weekly evaluations are presented in Table 1.

TABLE 1

Weed control efficacy of a *S. acidiscabies* extract containing thaxtomin A on different weed species.
Rating scale: 0 - control, 1 - 10% control, 2 - 25% control, 3 - 50% control, 4 - 75% control, 5 - 100% control.

| Weed | UTC | | | THAXTOMIN SOLUTION 0.5 mg/mL | | | THAXTOMIN SOLUTION 1.0 mg/mL | | |
|---|---|---|---|---|---|---|---|---|---|
| species | 7 DAYS | 14 DAYS | 21 DAYS | 7 DAYS | 14 DAYS | 21 DAYS | 7 DAYS | 14 DAYS | 21 DAYS |
| Dandelion | 0.0 | 0.0 | 0.0 | 2.0 | 2.3 | 4.0 | 2.0 | 2.0 | 3.7 |
| Nightshade | 0.0 | 0.0 | 0.0 | 2.7 | 2.2 | 2.3 | 2.7 | 2.0 | 2.3 |
| Lambsquarter | 0.0 | 0.0 | 0.0 | 2.0 | 2.0 | 2.0 | 2.0 | 2.0 | 2.0 |

TABLE 1-continued

Weed control efficacy of a *S. acidiscabies* extract containing thaxtomin A on different weed species.
Rating scale: 0 - control, 1 - 10% control, 2 - 25% control, 3 - 50% control, 4 - 75% control, 5 - 100% control.

| Weed | UTC | | | THAXTOMIN SOLUTION 0.5 mg/mL | | | THAXTOMIN SOLUTION 1.0 mg/mL | | |
|---|---|---|---|---|---|---|---|---|---|
| species | 7 DAYS | 14 DAYS | 21 DAYS | 7 DAYS | 14 DAYS | 21 DAYS | 7 DAYS | 14 DAYS | 21 DAYS |
| Ragweed | 0.0 | 0.0 | 0.0 | 1.0 | 0.5 | 0.0 | 1.0 | 0.5 | 0.0 |
| Velvetleaf | 0.0 | 0.0 | 0.0 | 1.7 | 1.0 | 1.0 | 2.0 | 1.0 | 0.3 |
| Bindweed | 0.0 | 0.0 | 0.0 | 1.0 | 1.0 | 0.0 | 1.2 | 1.0 | 0.0 |
| Mustard | 0.0 | 0.0 | 0.0 | 3.3 | 4.0 | 4.5 | 3.5 | 2.8 | 3.5 |
| Sunflower | 0.0 | 0.0 | 0.0 | 1.0 | 2.0 | 0.5 | 1.0 | 1.7 | 0.5 |
| Mallow | 0.0 | 0.0 | 0.0 | 1.0 | 1.0 | 1.0 | 1.2 | 1.0 | 1.0 |
| Pigweed | 0.0 | 0.0 | 0.0 | 3.5 | 4.0 | 4.0 | 4.2 | 3.0 | 3.7 |

The extract from a bacterial culture of *S. acidiscabies* with a thaxtomin A concentration of 0.5 mg/mL or higher showed good efficacy (>50%) against at least three of the most common broadleaf weed species (dandelion, mustard and pigweed) in both cereal and turf growing systems. Control of some weeds such as Black nightshade and Common lambsquarter was not complete but thaxtomin A even at the lower concentration (0.5 mg/mL) results in severe stunting of these weeds.

In this same study, no adverse effects are observed in grass species treated with either 0.5 or 1.0 mg/mL thaxtomin A. In all tested grass species, no phytotoxic effects were visible at even the higher thaxtomin A concentration.

Example 5

The combined effect of thaxtomin A and two commercial herbicides (Bipyribac-sodium formulated as Regiment and Lemongrass oil formulated as GreenMatch EX) on small-flower umbrella sedge and watergrass is tested in a field study using small (1-sq foot) plots. All single product treatments and tank mix combinations were sprayed at 57 gal per acre. Evaluation of % control was done 14 days after treatment and the results are presented in Table 2 below. Means in each column marked with the same letter in Table 2 are not statistically different from each other at $p<0.05$.

According to the results, lemongrass oil at 1.25% weight does not improve the efficacy of thaxtomin A (at 0.25 mg/mL) on sedge but it significantly increases the efficacy on grass weeds such as watergrass (field test) and sprangletop (greenhouse test).

TABLE 2

Effect of thaxtomin A alone and in combination with bispyribac-sodium and lemongrass oil on two rice weeds, small-flower umbrella sedge and watergrass.

| Treatment | Sedge control (%) | Watergrass control (%) |
|---|---|---|
| Thaxtomin 0.25 mg/mL | 95a | 5d |
| Thaxtomin 0.5 mg/mL | 100a | 5d |
| Bispyribac-sodium (12 g/acre) (12 g/acre) | 87.5a | 32.5a |
| Bispyribac-sodium ½ (6 g/acre) | 47.5c | 15c |
| Bispyribac-sodium ½ + Thaxtomin 0.5 mg/mL | 67.5b | 25ab |
| Bispyribac-sodium ½ + Thaxtomin 0.25 mg/mL | 55bc | 7.5c |
| Lemongrass oil 5% | 15d | 10c |
| Lemongrass oil 2.5% | 12.5d | 10c |
| Lemongrass oil 1.25% | 20d | 5d |

TABLE 2-continued

Effect of thaxtomin A alone and in combination with bispyribac-sodium and lemongrass oil on two rice weeds, small-flower umbrella sedge and watergrass.

| Treatment | Sedge control (%) | Watergrass control (%) |
|---|---|---|
| Lemongrass oil 1.25% + Thax 0.25 mg/mL | 100a | 10c |
| Lemongrass oil 1.25% + Thaxtomin 0.5 mg/mL | 100a | 20b |

According to the results, lemongrass oil at 1.25% does not improve the efficacy of thaxtomin A (at 0.25 mg/mL) on sedge but it significantly increases the efficacy on grass weeds such as watergrass (field test) and sprangletop. Thaxtomin A (at 0.5 mg/mL) improves the efficacy of an ALS inhibitor, bipyribac sodium; used at half label rate on both sedge and grasses.

Example 6

The efficacy of thaxtomin A derived from a liquid culture of *S. acidiscabies* is tested in a field study on rice using 4.9 sq-ft plots surrounded by a metal ring. Treatments with either thaxtomin A or thaxtomin A in combination with lemongrass oil (formulated as GreenMatch EX) or cyhalofop (formulated as Clincher CA) were done using a hand-held sprayer with a water volume corresponding to 57 gallons per acre. Rice (variety M209) was grown until maturity and harvested by hand for yield and weed count assessment. Results of yield (kg/ha), and numbers of redstem, small-flower umbrella sedge, and sprangletop in each plot are presented in Table 3 below.

TABLE 3

Effect of thaxtomin A alone and in combination with lemongrass oil and cyhalofop on rice yield and weed control.

| Treatment | Yield (kg/ha) | # of redstem | # of sedge | # of sprangletop |
|---|---|---|---|---|
| 1 | 7516b | 10.3 | 0.8a | 86.0a |
| 2 | 7876b | 0.5b | 1.0a | 76.0a |
| 3 | 9054ab | 0.3b | 0.5a | 69.3a |
| 4 | 11296a | 12.8a | 0.5a | 4.0b |

1. UTC;
2. Thaxtomin A (180 g/acre);
3. Lemongrass oil 1.25% + thaxtomin A (90 g/acre);
4. Cyhalofop (half label rate; 52 g/acre) + thaxtomin A (90 g/acre) + veg oil 2.5%

Means in each column marked with the same letter are not statistically different from each other at $p < 0.05$.

Results indicate that thaxtomin at 180 g/acre significantly reduced the number of sedges but had no effect on sprangletop or yield. When used at half rate (thaxtomin A 90 g/acre), a combination with lemongrass oil had better effect on sedges than a combination with cyhalofop (used at half label rate 52 g/acre). Good grass weed (sprangletop) control is achieved when thaxtomin (90 g/acre) is combined with cyhalofop at half the label rate—this combination also improves the yield significantly.

Example 7

Cyhalofop (2-[4-(4-cyano-2-fluorophenoxy)phenoxy] propanoic acid, butyl ester) is also mixed together with adjuvant containing ethyl oleate, polyethylene dialky ester and ethoxylated nonylphenol (2.5% v/v) and increasing concentrations of thaxtomin A (purified from the ATCC strain 49003) at concentrations 0.1, 0.2 and 0.4 mg/ml. The concentrations of the 2-[4-(4-cyano-fluorophenoxy)phenoxy]propanoic acid, butyl ester before dilution are 29.6% (2.38 lb/gal) and 21.7% (2 lb/gal), respectively. The effect of these mixtures on the growth of common water plantain, red stem, smallflower sedge and sprangletop is determined in the greenhouse. Similarly, rice plants of variety M104 are grown and tested for phytotoxic effects, and all plants are evaluated 7, 14, and 21 days after treatment. Results of from the study with cyhalofop formulated as Clincher CA at the 21-day evaluation point are presented in Table 4 below.

TABLE 4

Effect of thaxtomin A alone and with cyhalofop on rice yield and weed control

| Cyhalofop (6.5 oz/acre) + Thaxtomin A (mg/mL) | Redstem % control | Waterplantain % control | Sedge % control | Sprangletop % control |
|---|---|---|---|---|
| UTC | 0 | 0 | 0 | 0 |
| 0 - no thx A | 75 | 8 | 0 | 90 |
| 0.1 | 100 | 85 | 87 | 100 |
| 0.2 | 97 | 87 | 88 | 100 |
| 0.4 | 100 | 85 | 100 | 100 |

As a conclusion, Clincher CA (29.6% cyhalofop by weight) applied at half label rate (6.5 oz/acre) has good efficacy against grass weeds—not so good on broadleaves and poor on sedges. A combination of Clincher CA (cyhalofop) and thaxtomin A provides good control of all rice weeds tested in this study. Efficacy of thaxtomin A against grass weeds is substantially improved if combined with Clincher. Combination of thaxtomin A with Clincher CA did not cause phytotoxicity on rice at any tested concentration.

Example 8

Penoxsulam(2-(2,2-difluoroethoxy)-N-(5,8-dimethoxy[1,2,4]triazolo[1,5c]pyrimidin-2-yl)-6-trifluoromethyl)benzenesulfonamide) is mixed together with adjuvant containing ethyl oleate, polyethylene dialky ester and ethoxylated nonylphenol (2.5% v/v) and increasing concentrations of thaxtomin A (purified from the ATCC strain 49003) at concentrations 0.1, 0.2 and 0.4 mg/ml. The concentrations of the 2-[4-(4-cyano- -fluorophenoxy)phenoxy]propanoic acid, butyl ester or 2-(2,2-difluoroethoxy)-N-(5,8-dimethoxy[1,2,4]triazolo[1,5c]pyrimidin-2-yl)-6-trifluoromethyl)benz enesulfonamide before dilution are 29.6% (2.38 lb/gal) and 21.7% (2 lb/gal), respectively. The effect of these mixtures on the growth of common water plantain, red stem, smallflower sedge and sprangletop is determined in the greenhouse. Similarly, rice plants of variety M104 are grown and tested for phytotoxic effects, and all plants are evaluated 7, 14, and 21 days after treatment.

Example 9

A strain of *S. acidiscabies* was grown in oat bran broth for 5 days (25° C., 200 rpm). The whole cell broth was extracted using XAD resin, and the dried crude extract was resuspended in 4% ethanol and 0.2% non-ionic surfactant at a concentration of 10 mg/mL. The diluted extracts containing 0.2 and 0.4 mg thaxtomin A per mL were tested on three weed species (redstem; *Ammania* spp., smallflower umbrella sedge; *Cyperus difformis* and sprangletop: *Leptochloa uninervia*). Other treatments included sarmentine at 2.5 and 5.0 mg/mL, and a combination treatment containing 0.2 mg thaxtomin A and 2.5 mg sarmentine per mL. Each treatment was applied in three replicates. Treated plants were kept in a greenhouse under 12 h light/12 h dark conditions. Results from an evaluation performed 25 days after treatment are presented in Table 5.

TABLE 5

Efficacy of herbicidal treatments using thaxtomin A (0.2 and 0.4 mg/mL) or sarmentine (2.5 or 5.0 mg/mL) alone or in combination (0.2 + 2.5 mg/mL) to control broadleaf, sedge and grass weeds in a greenhouse study.

| Treatment | Control of redstem (%) | Control of sedge (%) | Control of sprangletop (%) |
|---|---|---|---|
| UTC | 0a | 0a | 0a |
| Thaxtomin A 0.2 mg/mL | 5.0b | 48.3b | 8.3ab |
| Thaxtomin A 0.4 mg/mL | 11.7c* | 91.7d | 10.0b |
| Thaxtomin 0.2 + Sarmentine 2.5 mg/mL | 11.7c* | 61.7c | 73.3c |
| Sarmentine 2.5 mg/mL | 0a | 8.3a | 80.0c |
| Sarmentine 5.0 mg/mL | 2.5ab | 6.7a | 92.3d |

*stunted. In a column, Means followed by the same letter are not statistically different from each other at $p < 0.05$.

Thaxtomin A at the highest concentration of 0.4 mg/mL provides excellent control of sedge but poor control of the grass weed (sprangletop). When combined with sarmentine, the efficacy against grass weeds improves significantly. Also, efficacy against sedge is improved with the combination treatment compared with the single application of thaxtomin A alone at the corresponding concentration. In this study, the control of the broadleaf weed (redstem) is poor with all treatments.

Example 10

Bialaphos is produced by bacteria *Streptomecyes* spp. and its synthesized active ingredient glufosinate is marketed as Rely® 200 (Bayer CropScience, Research Triangle Park, N.C.). Bialaphos has a non-selective property and inhibits the activity of glutamine synthetase, an enzyme involved in the synthesis of the amino acid glutamine.

The MBI-005 and bialaphos were prepared at various concentrations either as single ingredients or in combination with bialaphos. The treatments were applied at approximately ⅔ ml per replicate with a hand-help spray nozzle to barnyard grass or sedge. There were 3 replicates per treatment which were randomized after spray and were kept in a greenhouse at 25° C. for evaluation of phytotoxicity (% control).

When MBI-005 was mixed with bialaphos, the efficacy was increased several times more than when they were used alone (Table 6, 7, and 8). At higher rates of the mixtures, 100% control was achieved (Table 8). Synergy was observed when bialaphos at 0.178 mg/mL was mixed with MBI-005 at 0.25 mg/mL, and about 42% efficacy was achieved when the rate of bialaphos was increased close to 1.0 mg/mL from 10% control with bialaphos alone (Table 7).

TABLE 6

Effects of bialaphos, MBI-005 (thaxtomin A), and the combinations of bialaphos with MBI-005 in controlling barnyard grass.

| Treatment | Bialaphos (mg/mL) | MBI-005 (mg/L) | % Control (14 days) | E/Ee# |
|---|---|---|---|---|
| Untreated Control (deionized water) | | | 0.0 a* | |
| Bialaphos | 0.089 | | 0.0 a | |
| Bialaphos | 0.178 | | 0.0 a | |
| Bialaphos | 0.356 | | 0.0 a | |
| Bialaphos | 0.534 | | 0.0 a | |
| Bialaphos | 0.712 | | 0.0 a | |
| Bialaphos | 0.890 | | 1.3 ab | |
| Bialaphos | 1.068 | | 5.0 abc | |
| MBI-005 (thaxtomin A) | | 0.25 | 1.3 ab | |
| Bialaphos + MBI-005 | 0.089 | 0.25 | 1.3 ab | 1.0 |
| Bialaphos + MBI-005 | 0.178 | 0.25 | 3.8 abc | 3.0 |
| Bialaphos + MBI-005 | 0.356 | 0.25 | 11.9 c | 9.5 |
| Bialaphos + MBI-005 | 0.534 | 0.25 | 29.4 d | 23.5 |
| Bialaphos + MBI-005 | 0.712 | 0.25 | 34.4 d | 27.5 |
| Bialaphos + MBI-005 | 0.890 | 0.25 | 59.4 e | 23.9 |
| Bialaphos + MBI-005 | 1.068 | 0.25 | 62.5 e | 10.1 |

*Treatment means in each column marked with the same letter are not statistically different at LSD at p = 0.05 level.
#Synergy is calculated from Colby's formula (Colby, 1967. Weeds 15: 20-22): Ee = X + Y − (XY/100) (Where E is the observed efficacy of product A + B, Ee is expected efficacy of A + B, and X and Y are the efficacy of product A or B when used alone. If E/Ee <1 the combination is antagonistic; if E/Ee = 1 the combination is additive; if E/Ee >1 the combination is synergistic).

TABLE 7

Effects of bialaphos, MBI-005 (thaxtomin A), and the combinations of bialaphos with MBI-005 in controlling barnyard grass.

| Treatment | Bialaphos (mg/mL) | MBI-005/011 (mg/mL) | % Control (14 days) | E/Ee |
|---|---|---|---|---|
| Untreated Control (deionized water) | | | 0.0 a* | |
| Bialaphos | 0.18 | | 6.7 bc | |
| Bialaphos | 0.53 | | 3.3 ab | |
| Bialaphos | 1.07 | | 10.0 c | |
| MBI-005 (thaxtomin A) | | 0.25 | 6.7 bc | |
| Bialaphos + MBI-005 | 0.18 | 0.25 | 5.0 abc | 0.4 |
| Bialaphos + MBI-005 | 0.53 | 0.25 | 25.0 d | 2.6 |
| Bialaphos + MBI-005 | 1.07 | 0.25 | 41.7 e | 2.6 |

*Treatment means in each column marked with the same letter are not statistically different with LSD test at p = 0.05 level

TABLE 8

Effects of bialaphos, MBI-005 (thaxtomin A), and the combinations of bialaphos with MBI-005 or MBI-011 in controlling barnyard grass.

| Treatment | Bialaphos (mg/mL) | MBI-005 (mg/mL) | % Control (7 days) | % Control (14 days) | E/Ee (7 days) |
|---|---|---|---|---|---|
| Untreated Control (deionized water) | | | 0.0 a* | 0.0 a | |
| Bialaphos | 1.1 | | 5.0 ab | 3.7 a | |
| Bialaphos | 1.4 | | 10.8 b | 23.3 b | |
| Bialaphos | 1.8 | | 62.5 c | 66.7 c | |
| MBI-005 (thaxtomin A) | | 0.38 | 6.7 ab | 21.7 b | |
| Bialaphos + MBI-005 | 1.1 | 0.38 | 87.5 d | 100.0 d | 7.7 |
| Bialaphos + MBI-005 | 1.4 | 0.38 | 87.5 d | 100.0 d | 5.2 |
| Bialaphos + MBI-005 | 1.8 | 0.38 | 87.5 d | 100.0 d | 1.3 |

*Treatment means in each column marked with the same letter are not statistically different with LSD at p = 0.05 level.

Example 11

The test species barnyard grass, ragweed, sedge, and broad-leaf mustard were used for the valuation of synergy between MBI-005 and the rice herbicides clomazone, penoxsulam, cyhalofop, fenoxaprop-p-ethyl, bispyribac-sodium, thiobencarb, and propanil.

The common turf weeds dandelion and plantain were used in testing for synergy between MBI-005 and 2, 4—or dicamba, two common turf herbicides.

Three other herbicides commonly used for field crops, glyphosate, glufosinate, synthetic version of bialaphos, and mesotrione were also tested for synergy with MBI-005 on crabgrass and ragweed.

There were 3 replicates per treatment which were sprayed with approximately ⅔ ml per replicate. The treatments were completely randomized and kept in a greenhouse at 25° C. The efficacy was rated at 7 and 14 days post treatment. The results are shown in Table 9 to 11. For barnyard grass control, MBI-005 had synergistic effects when combined with clomazone, (penoxsulam, bispyribac-sodium, thiobencarb, and propanil (Table 9). MBI-005 had additive effects when combined with cyhalofop, and fenoxaprop-p-ethyl (Table 10).

MBI-005 showed great synergy with glyphosate for controlling ragweed and also showed synergy with both turf herbicides. The synergistic effect of MBI-005 with glufosinate (synthetic bialaphos) (Table 11) on crabgrass was likely less since the rate of MBI-005 was too low.

TABLE 9

Summary of synergistic or additive effects between MBI-005 (thaxtomin A) and commercial products for rice weed control. The data are means of percentage control of three replicates 14 days post treatment.

| Active Ingredient | Test Species | Product Rate (mg/mL) | MBI-005 Rate (mg/mL) | % Control Product | % Control MBI-005 | % Control Product + MBI-005 | E/Ee |
|---|---|---|---|---|---|---|---|
| clomazone | Barnyard grass | 0.513 | 0.25 | 37.5 | 28.3 | 91.7 | 1.7 |
| | Mustard | 0.513 | 0.25 | 25.0 | 58.3 | 70.8 | 1.0 |
| | Sedge | 0.501 | 0.02 | 0.0 | 37.5 | 50.0 | 1.3 |

TABLE 9-continued

Summary of synergistic or additive effects between MBI-005 (thaxtomin A) and commercial products for rice weed control. The data are means of percentage control of three replicates 14 days post treatment.

| Active Ingredient | Test Species | Product Rate (mg/mL) | MBI-005 Rate (mg/mL) | % Control Product | % Control MBI-005 | % Control Product + MBI-005 | E/Ee |
|---|---|---|---|---|---|---|---|
| penoxsulam | Barnyard grass | 0.051 | 0.125 | 25.0 | 17.5 | 75.0 | 2.0 |
| | Sedge | 0.047 | 0.01 | 66.7 | 20.0 | 87.5 | 1.2 |
| cyhalofop | Mustard | 0.051 | 0.125 | 11.7 | 13.3 | 15.0 | 0.6 |
| | Sedge | 1.176 | 0.01 | 3.3 | 20.0 | 8.3 | 0.4 |
| fenoxaprop-p-ethyl | Barnyard grass | 0.006 | 0.25 | 91.7 | 66.7 | 87.5 | 0.9 |
| | Mustard | 0.006 | 0.125 | 0.0 | 45.8 | 33.3 | 0.7 |
| | Sedge | 0.116 | 0.02 | 0.0 | 70.8 | 66.7 | 0.9 |
| bispyribac-sodium | Barnyard grass | 0.032 | 0.125 | 0.0 | 3.3 | 62.5 | 18.8 |
| | Mustard | 0.0216 | 0.25 | 53.3 | 37.5 | 95.8 | 1.4 |
| | Ragweed | 0.0216 | 0.125 | 5.0 | 23.3 | 50.0 | 1.8 |
| thiobencarb | Barnyard grass | 1.743 | 0.25 | 41.7 | 41.7 | 79.2 | 1.2 |
| | Mustard | 1.743 | 0.125 | 10.0 | 54.2 | 54.2 | 0.9 |
| | Sedge | 3.15 | 0.02 | 58.3 | 37.5 | 70.8 | 1.0 |
| propanil | Barnyard grass | 0.365 | 0.125 | 32.5 | 10.0 | 79.2 | 2.0 |
| | Mustard | 0.036 | 0.25 | 1.67 | 58.3 | 50.0 | 0.9 |

TABLE 10

Summary of synergistic or additive effects between MBI-005 (thaxtomin A) and commercial products for turf weed control. The data are means of percentage control of three replicates 14 days post treatment.

| Active Ingredient | Weed Species | Product Rate (mg/mL) | MBI-005 Rate (mg/mL) | % Control Product | % Control MBI-005 | % Control Product + MBI-005 | E/Ee |
|---|---|---|---|---|---|---|---|
| 2,4-D | Dandelion | 0.176 | 0.1 | 25.0 | 20.0 | 91.7 | 2.3 |
| | Plantain | 2.340 | 0.24 | 50.0 | 25.0 | 83.3 | 1.3 |
| dicamba | Dandelion | 0.121 | 0.1 | 45.8 | 20.0 | 75.0 | 1.3 |
| | Plantain | 6.025 | 0.12 | 50.0 | 10.0 | 79.2 | 1.4 |

TABLE 11

Summary of synergistic or additive effects between MBI-005 (thaxtomin A) and commercial products with broad spectrum. The data are means of percentage control of three replicates 14 days post treatment.

| Active Ingredient | Weed Species | Product Rate (mg/mL) | MBI-005 Rate (mg/mL) | % Control Product | % Control MBI-005 | % Control Product + MBI-005 | E/Ee |
|---|---|---|---|---|---|---|---|
| glyphosate | Crabgrass | 0.754 | 0.125 | 45.8 | 28.3 | 83.3 | 1.4 |
| | Ragweed | 2.198 | 0.125 | 15.0 | 6.7 | 29.2 | 1.4 |
| glufosinate | Crabgrass | 0.151 | 0.125 | 83.3 | 20.0 | 75.0 | 0.9 |
| (bialaphos) | Ragweed | 0.194 | 0.125 | 22.5 | 37.5 | 75.0 | 1.5 |
| mesotrione | Crabgrass | 0.24 | 0.125 | 62.5 | 24.2 | 75.0 | 1.1 |
| | Ragweed | 0.96 | 0.125 | 25.0 | 15.0 | 45.8 | 1.3 |

Although this invention has been described with reference to specific embodiments, the details thereof are not to be construed as limiting, as it is obvious that one can use various equivalents, changes and modifications and still be within the scope of the present invention. Various references are cited throughout this specification, each of which is incorporated herein by reference in its entirety.

CITED REFERENCES

Beauséjour, J., C. Goyer, et al. (1999). "Production of thaxtomin A by *Streptomyces scabies* strains in plant extract containing media." *Can J Microbiol* 45: 764-768.

Duke, S. O., S. R. Baerson, et al. (2003). "United States Department of Agriculture-Agricultural Research Service research on natural products for pest management." *Pest Manag Sci* 59: 708-717.

Duke, S. O., F. E. Dayan, et al. (2000). "Natural products as sources of herbicides: current status and future trends." *Weed Research* 40: 99-111.

Fry, B. A. and R. Loxia (2002). "Thaxtomin A: Evidence for a plant cell wall target." *Physiological and Molecular Plant Pathology* 60: 1-8.

Gerwick, B. C., P. R. Graupner, et al. (2005). Methylidene mevalonates and their use as herbicides. U. p. 7393812: 16.

Healy, F. G., M. J. Wach, et al. (2000). "The txtAB genes of the plant pathogen *Streptomyces* acidiscabies encode a peptidesynthetase required for phytotoxin thaxtomin A prodcution and pathogenicity." *Molecular Microbiology* 38: 794-804.

Hiltunen, L. H., I. Laakso, et al. (2006). "Influence of thaxtomins in different combinations and concentrations on growth of micropropagated potato shoot cultures." *J Agric Food Chem* 54: 3372-3379.

Hoagland, R. E. (2001). "Microbial allelochemicals and pathogens as bioherbicidal agents." *Weed Technology* 15: 835-857.

Kang, Y., S. Semones, et al. (2008). Methods of controlling algae with thaxtomin and thaxtomin compositions. USA, Novozymes Biologicals, Inc.

King, R. R., C. H. Lawrence, et al. (1992). "Chemistry of phytotoxins associated with *Streptomyces scabies*, the causal organism of potato common scab." *J. Agric. Food Chem* 40: 834-837.

King, R. R., C. H. Lawrence, et al. (1989). "Isolation and characterization of phytotoxin associated with *Streptomyces scabies*." Journal of the Chemical Society, Chemical Communications 13: 849-850.

King, R. R., C. H. Lawrence, et al. (2003). "More chemistry of the thaxtomin phytotoxins." *Phytochemistry* 64: 1091-1096.

King, R. R., C. H. Lawrence, et al. (2001). "Herbicidal properties of the thaxtomin group of phytotoxins." *J Agric Food Chem* 49: 2298-2301.

Loxia, R., R. A. Bukhalid, et al. (1995). "Differential production of thaxtomins by pathogenic *Streptomyces* species in vitro " *Phytopathology* 85: 537-541.

What is claimed is:

1. An herbicidal composition comprising at least two herbicides wherein a first herbicide is thaxtomin, wherein said thaxtomin has the structure

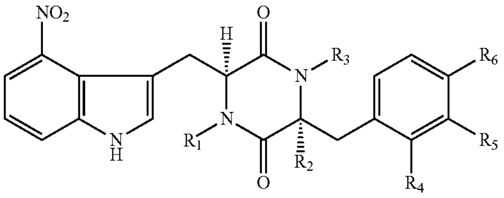

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, and combinations thereof;

and a second herbicide is bialaphos, wherein the first and second herbicides are present in a synergistic amount to control barnyard grass or ragweed, wherein the synergistic amount is measured by determining E/Ee, and E/Ee is at least 1.3.

2. The composition according to claim 1, wherein said composition further comprises an adjuvant, a non-ionic surfactant and/or an organic solvent.

3. The composition according to claim 1, wherein said composition further comprises a non-ionic surfactant and/or an aliphatic alcohol.

4. The composition of claim 1, wherein said thaxtomin is thaxtomin A.

5. The composition of claim 1, wherein the first and second herbicides are present in a synergistic amount to control ragweed by at least 75%.

6. The composition of claim 1, wherein E/Ee is at least 2.6.

7. The composition of claim 1, wherein E/Ee is at least 7.7.

8. A method for modulating growth of barnyard grass or ragweed comprising applying to said barnyard grass or ragweed or to the soil of said barnyard grass or ragweed an amount of the composition of claim 1.

9. The method of claim 8, wherein growth of barnyard grass is modulated.

10. The method of claim 8, wherein growth of ragweed is modulated.

11. The method of claim 8, wherein the thaxtomin is thaxtomin A.

12. The method of claim 10, wherein the first and second herbicides are present in an synergistic amount to control ragweed by at least 75%.

13. The method of claim 8, wherein E/Ee is at least 2.6.

14. The method of claim 8, wherein E/Ee is at least 7.7.

15. The method of claim 8, wherein said composition further comprises an adjuvant, a non-ionic surfactant and/or an organic solvent.

16. The method of claim 8, wherein said composition further comprises a non-ionic surfactant and/or an aliphatic alcohol.

* * * * *